United States Patent [19]
Fujieda et al.

[11] Patent Number: 5,212,507
[45] Date of Patent: May 18, 1993

[54] APPARATUS FOR MEASURING CORNEA SHAPE

[75] Inventors: Masanao Fujieda, Toyohashi; Akihiro Hayashi, Toyokawa; Toshiya Hino, Toyohashi, all of Japan

[73] Assignee: Nidek Co., Ltd., Gamagori, Japan

[21] Appl. No.: 646,908

[22] Filed: Jan. 28, 1991

[30] Foreign Application Priority Data

Jan. 29, 1990 [JP] Japan .................................. 2-19966

[51] Int. Cl.⁵ .............................................. A61B 3/10
[52] U.S. Cl. ..................................... 351/212; 351/247
[58] Field of Search ................. 351/212, 247; 356/376

[56] References Cited

U.S. PATENT DOCUMENTS 4,312,574  1/1982  Wilms ............................. 351/212 X
4,660,946  4/1987  Nakamura et al. ................. 351/212

FOREIGN PATENT DOCUMENTS 38-181735  7/1963  Japan .
19896  4/1989  Japan .

*Primary Examiner*—Rodney B. Bovernick
*Attorney, Agent, or Firm*—Nikaido Marmelstein Murray & Oram

[57] ABSTRACT

An apparatus for measuring a corneal shape includes a projecting device projecting a set of point sources, which are substantially on a same circle, onto a cornea. A detecting optical system defects the positions of the point sources projected onto the cornea by the projecting device. A selecting device selects a plurality of the corneal reflection images detected by the detecting optical system, each of which consists of at least 3 points forming a part of the circle. A calculating device obtains a part of the corneal shape by presuming an ellipse containing the points of each selected group in the corneal reflection images. A displaying device displays the corneal shape based on the results obtained by the calculating device.

6 Claims, 4 Drawing Sheets

APPARATUS FOR MEASURING CORNEA SHAPE

FIELD OF THE INVENTION

The present invention relates to an apparatus for measuring a cornea-shape of a patient.

BACKGROUND OF THE INVENTION

There is known an apparatus for measuring a cornea shape manually, in which predetermined point source, projected onto a cornea and prisms, etc., are disposed within an optical path of an observing optical system are moved as well as rotated while observing the corneal reflection images of the point sources, so that the images are in a predetermined condition. The radius of curvature of the cornea is measured based on the amount of movement as well as the amount of rotation thus obtained.

Recently photoelectric type apparatuses for measuring a corneal shape are widely utilized in lieu of the conventional manual measuring apparatus. Various measuring methods of the photoelectric type measuring apparatus are proposed. Common to these methods are the following features. A set of point sources which are substantially on a same circle (including a ring aperture) is projected onto a cornea. The corneal reflection images of the point sources are detected by means of one or a plurality of one-dimentional detecting means or two-dimensional detecting means. Supposing that the corneal reflection images detected by the detecting means are on a single ellipse the corneal shape is calculated on the basis thereof (subjecting it to operations such as connections, etc.).

The applicants of the present invention have also disclosed, in JP-B-Hei 1-19896, an apparatus for measuring a corneal shape comprising: ①projecting means for projecting point sources including 2 point sources which are placed in symmetry with respect to the optical axis of the measuring optical system and at least another one point source which is placed on a same circle as that of the 2 point sources onto a cornea; ② detecting means for detecting the point sources reflected by the cornea; ③ an imaging optical system which focuses the corneal reflection images of the point sources at least in the direction detected by the detecting means; ④ calculating means which calculates the coordinates of the center of the ellipse containing the images of the point sources from the detected positions of the 2 points which are symmetric with respect to the optical axis of the measuring optical system, and then calculates the shape of the ellipse containing the images of the point sources by calculating coordinates of the center and the coordinates of the 3 points in the corneal reflection image.

The photoelectric-type apparatus for measuring a corneal shape described above has a merit that is available to measure a corneal shape automatically independent of skills of the examiner. Although in the above-described measuring method according to the prior art, a corneal shape is measured presuming that a cornea has a uniform toric surface however, a cornea does not necessarily have a uniform toric surface. Therefore an apparatus having the construction as described above has a problem in that a corneal shape is measured and displayed as if it had a uniform toric surface.

SUMMARY OF THE INVENTION

The object of the present invention is to provide an apparatus for measuring a corneal shape accurately.

The apparatus for measuring the shape of cornea according to the present invention has features as described below.

An apparatus for measuring a corneal shape includes a projecting device for projecting a set of point sources, which are substantially on a same circle, onto a cornea. A detecting optical system detects the positions of the point sources projected onto the cornea by the projecting device. A selecting device for selects a plurality of the corneal reflection images detected by the detecting optical system. Each of the images consists of at least 3 points forming a part of the and change circle. A calculating device obtains a part of the corneal shape by presuming an ellipse containing the points of each selected group in the corneal reflection images. A display-ing device displays the corneal shaped based on calculation results obtained by the calculating device.

In a further embodiment the projecting device projects at least 4 point sources or a circular slit onto the cornea.

The at least 4 point sources are comprised of 2 pairs of point sources which are symmetric with respect to an optical axis.

Also, the point sources are arranged on the upper, lower, left and right sides of an examined eye so that lines passing through different pairs, which are opposite to each other, are perpendicular to each other.

The detecting optical system is composed of a two-dimensional detecting device or two one-dimensional detecting devices located at positions intersecting each other.

An alarm is displayed when the difference arising in the partial measurement of the corneal shape is larger than a predetermined value.

DETAILED DESCRIPTION OF THE PREFERRED EMBODIMENTS

One preferred embodiment of the present invention will be described hereunder with reference to the accompanying drawings.

Figure 1:
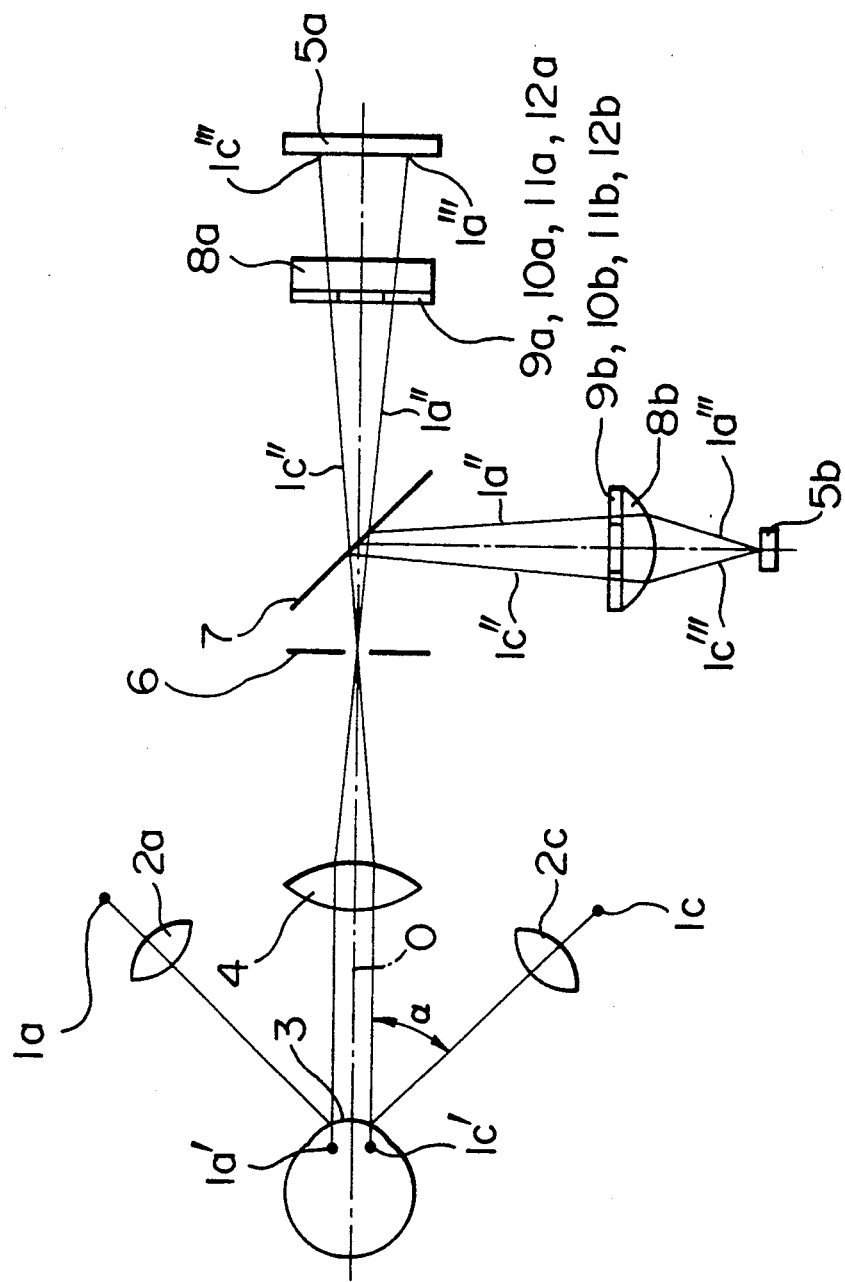
FIG. 1 is a scheme of optical construction indicating the outline of an embodiment of the present invention.

FIG. 1 is a schematic view showing the constitution of the optical system of one embodiment of the present invention. Since the scheme indicating the constitution of the optical system in the present embodiment is almost identical to that described in JP-B-Hei 1-19896, detailed explanation thereof will be omitted.

Reference numerals 1a, 1b, 1c and 1d (1b and 1d are not indicated in the FIG.) are point sources such as light emitting diodes, etc., which are disposed with an interval of 90° around the optical axis of the measuring optical system. The light beams emitted from the point sources 1a, 1b, 1c and 1d are respectively collimated into parallel light beams by collimator lenses 2a, 2b, 2c and 2d (2b and 2d are not indicated in the figure.), whereafter they are projected the cornea 3 of a patients eye at the angle of α from the optical axis of the measuring optical system, The projected light of the point sources 1a, 1b, 1c and 1d forms the corneal reflection images 1a', 1b', 1c', 1d'.

The imaging lens 4 is disposed at such a position that the detection planes of one-dimensional detecting devices 5a, 5b and the corneal reflection images 1a; 1b; 1c' and 1d' are interchangeable after passing through a telecentric diaphragm 6 at the image focal point of the imaging lens 4. The light beam passing though the telecentric diaphragm 6 is divided into 2 by a beam splitter 7.

Further, convex cylindrical lenses 8a and 8b are disposed between the telecentric diaphragm 6 and the one-dimensional detecting devices 5a, 5b so that the axis thereof corresponds to the direction detected by the one-dimensional detecting devices 5a and 5b, respectively. The focussing distance of the convex, cylindrical lens 8a and 8b is infinite in the plane of the cylindrical axis, and the focussing distance, is set to be as the distance where the telecentic diaphragm 6 and the one-dimensional detecting devices 5a and 5b are substantially conjugated with the convex cylindrical lenses 8a and 8b in the plane perpendicular to the cylindrical axis. The one-dimensional detecting devices 5a and 5b are disposed so that they are perpendicular to each other.

Figure 2:
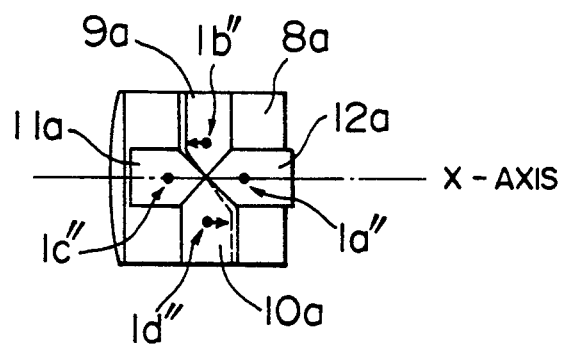
FIG. 2 is a front view showing a cylindrical lens used in the first embodiment stated above.

The prisms 9a, 10a and the plane glasses 11a, 12a are joined on the cylindrical lens 8a, as indicated in FIG. 2. The prisms 9a and 10a are disposed such that the light beams 1b" and 1d" from the corneal reflection images 1b' and 1d' are separated from each other on the one-dimensional detecting device 5a, and refract the light beams 1b" and 1d" toward the X-axis, therefore even if all the four point sources 1a, 1b, 1c and 1d are illuminated simultaneously, it is possible to detect each position of the corneal reflection images 1a', 1b', 1c', and 1d' in the direction of the X-axis. Similarly the prisms 9b, 10b, plane glasses 11b, 12b are joined on the cylindrical lens 8b.

The plane glasses 11a, 12a, 11b and 12b are disposed for the purpose of compensating the optical path length and have the same optical thickness as that of the prisms 9a, 10a, 9b and 10b.

Figure 3:
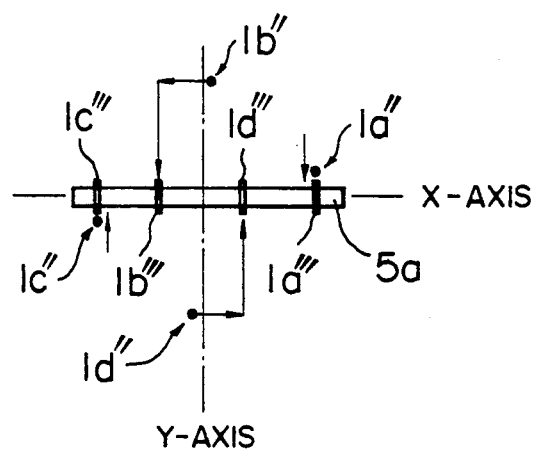
FIGS. 3 and 4 are front views showing different one-dimensional position detecting elements used in the first embodiment stated above.
Figure 4:
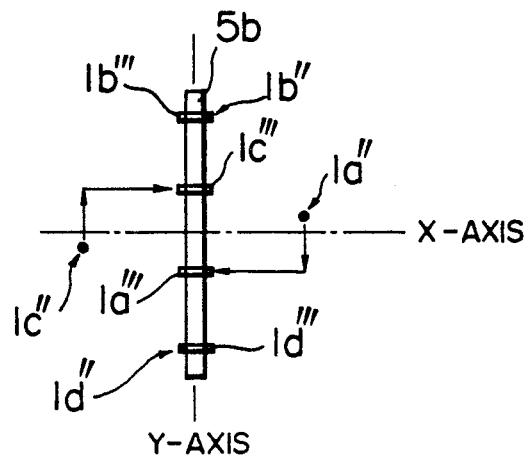

In such a construction, the light beams 1a", 1b"', 1c" and 1d"' from the corneal reflection images 1a', 1b', 1c' and 1d' are deflected onto the one-dimensional detecting devices 5a and 5b by the prism function of the convex cylindrical lenses 8a and 8b respectively and at the same time they are separated from each other by the prisms 9a, 10a, 9b and 10b. Accordingly, as indicated in FIGS. 3 and 4, the corneal reflection images 1a', 1b', 1c' and 1d' are focussed on the one-dimensional detecting devices 5a and 5b in the form of images 1a''', 1b''', 1c'''' and 1d'''' elongated in the direction perpendicular to the detection direction of each of the one-dimensional detecting devices 5a and 5b on a length corresponding to the size of the telecentric diaphragm 6 of the corneal reflection images.

The positional coordinates 1a', 1b', 1c' and 1d' are obtained by correcting results obtained by means of the one-dimensional detecting devices 5a and 5b, taking influences of optical magnifying power and the prisms into account.

Next calculations of the corneal shape based on the positional coordinates of the corneal reflection images 1a', 1b', 1c' and 1d' will be explained. Four groups comprising 3 points of [A',B',C'], [D',A',B'], [B',C',D'] and [D',A',C'] are obtained, in the corneal reflection images 1a', 1b', 1c' and 1d' (hereinbelow referred to by A', B', C' and D' respectively for the sake of convenience). For each of these groups an ellipse containing the 3 points is presumed and the corneal shape is measured for each of the groups.

Next, an example of the calculation method for measuring the corneal shape for each of the groups will be shown.

Figure 5:
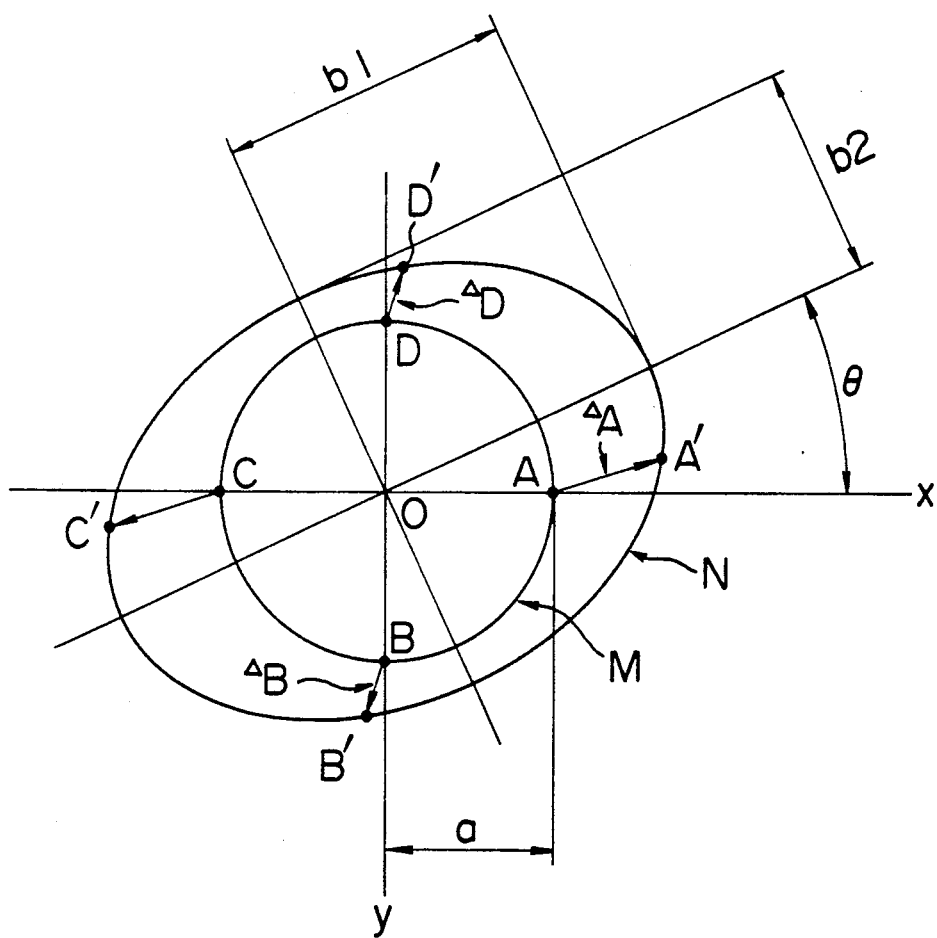
FIG. 5 is a front view of an image formed on a cornea, indicating the principle of measurement of the present invention.

It is supposed that a circular slit is projected onto the cornea. In the case where the cornea is a spheric surface, a circle M on the detection plane having a radius a is obtained, while an ellipse N having a major radius b1 and a minor radius b2 is obtained in the case where the cornea is a toric surface (refer to FIG. 5). Here it is supposed that the points A, B, C and D on the circle M correspond to A', B', C' and D' on the ellipse N respectively. Further, it is supposed that the ellipse N is inclined with respect to the X-axis by $\theta$ around the origin and that the (x,y) components of the displacement from A to A' are represented by ($\Delta Ax$) and ($\Delta Ay$), respectively, and the (x,y) components of the displacement from B to B' are represented by ($\Delta Bx$) and ($\Delta By$), respectively.

Then the following relationships are valid;

$$\Delta Ax = b1 \cos^2\theta + b2 \sin^2\theta - a \qquad (1)$$

$$\Delta Ay = (b1-b2) \sin\theta \cos\theta \qquad (2)$$

$$\Delta Bx = (b1=b2)\sin\theta \cos\theta \qquad (3)$$

$$\Delta By = b1 \sin^2\theta + b2 \cos^2\theta - a \qquad (4)$$

By using these relationships b1, b2 and $\theta$ can be given by the following formulas;

$$b1 = \frac{\Delta By + \Delta Ax + 2a + \sqrt{(\Delta By - \Delta Ax)^2 + 4\Delta Bx^2}}{2} \qquad (5)$$

$$b2 = \Delta By + \Delta Ax + 2a - b1 \qquad (6)$$

$$\theta = \frac{1}{2} \sin^{-1}\left(\frac{2\Delta Bx}{b1 - b2}\right) \qquad (7)$$

The corneal shape in the range [A',B',C'] is measured by detecting the coordinates X and Y of the points A', B' and C' formed by the cornea whose shape is unknown, using the formulas described above.

At first, the coordinates X and Y of the points A, B and C on the basic circle M are previously stored and the central point of the two points A' and C' is obtained, so that the origin O is determined, the basic circle M is that the reflection images of the point sources projected onto the basic sphere are focussed on the detection plane. $\Delta Ax$, $\Delta Ay$, $\Delta Bx$ and $\Delta y$ are calculated base on origin O and the ellipse is determined by using the formulas (5), (6) and (7).

Since the relation between the ellipse and the toric corneal shape has been known widely, although detailed explanation thereof is omitted, it is possible to obtain the radius of curvature in the range [A',B',C'] and the radius of curvature corresponding to the major radius and the minor radius, based on the specified ellipse.

In the same way calculations are executed for every group of [D',A',B'], [B',C',D']and [D',A',C'].

Figure 6:
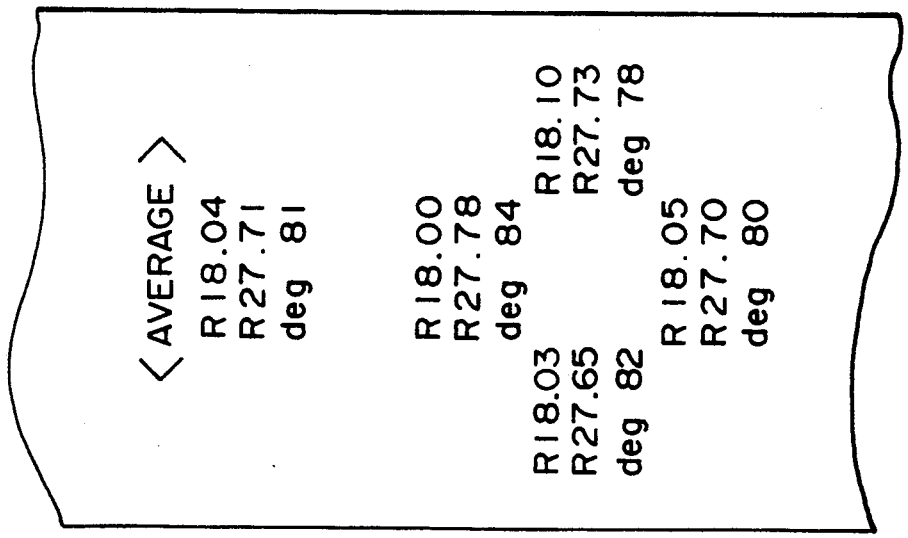

The corneal shape thus obtained is e.g. printed as indicated in FIG. 6, or displayed on a monitor. By printing or displaying the measured data in this manner, it is possible to indicate whether the cornea has a toric surface, that is, the degree of irregular astigmatism of an eye. If there is difference between different sets of measured data, which is larger than the predetermined value the caution thereof is indicated on the data in order to call upon the examiner to pay attention specifically thereto. In FIG. 6 the measured data indicated in the upper portion shows the average value of each part of the cornea.

Figure 7:
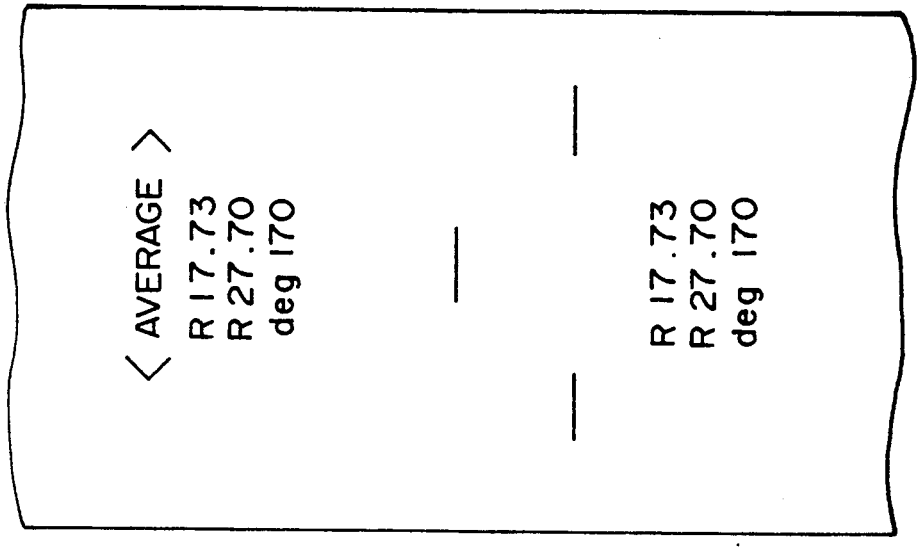
FIGS. 6 and 7 are front views of recording sheets indicating measurement results.

FIG. 7 shows an example of the printed record in which only one set of measured data is indicated. This means that one point source in the upper portion the four is interrupted by eyelashes, etc. so that the light beam emitted from the light source has not reached the one-dimentional position detecting devices 5a and 5b.

Although in the above embodiment 4 point sources are used, the present invention is not limited thereto. It is a matters of course that the technical idea is included in the present invention by which a set of more than four point sources which are substantially on a same circle (it may be a circular shaped image) is projected onto a cornea and the corneal shape is analysed for each part of the cornea using partial measured data on the corneal reflection images of point sources.

Further it is well known that there are various modifications for the calculation process for calculating the corneal shape and it is obvious that the present invention doesn't restrict such a calculation process itself.

As explained above, according to the present invention, it is possible to judge by means of a simple construction where a cornea has a toric surface and to indicate the degree thereof.

We claim:

1. An apparatus for measuring a corneal shape comprising:
    projecting means for projecting, onto a cornea, a set of at least four point light sources in a form of parallel light beams, which are substantially on a same circle, around an optical measuring system;
    detecting optical system means for detecting positions of said at least four point light sources projected onto and reflected by the cornea by said projecting means;
    means for grouping a plurality of sets of combinations of said at least four point light sources reflected by the cornea, each set of combinations containing at least three of said point light sources and for sequentially extracting positions of corneal reflection images of the respective sets detected by said detecting means;
    means for determining a part of a corneal shape, based on an elliptical shape, by connecting the extracted positions of the respective sets of corneal reflection images; and
    displaying means for displaying the corneal shape, based on the determination of each part of the corneal shape determined by said determining means.

2. An apparatus for measuring the corneal shape according to claim 1, wherein said at least four point sources are comprised of two pairs of point sources which are symmetric with respect to an optical axis.

3. An apparatus for measuring the corneal shape according to claim 2, wherein said point sources are arranged on upper, lower, left and right sides of an examined eye so that lines passing through a different two, which are opposite to each other, are perpendicular to each other.

4. An apparatus for measuring the corneal shape according to claim 1, wherein said detecting optical system means is composed of a two-dimensional detecting device or two one-dimensional detecting devices located at positions intersecting each other.

5. An apparatus for measuring the corneal shape according to claim 1, wherein an alarm is displayed when a difference arising the partial measurement of corneal shape is larger than a predetermined value.

6. A method for measuring a corneal shape comprising the steps of:
    projecting a set of at least four point light sources in a form of parallel light beams, which are substantially on a same circle, onto a cornea;
    detecting positions of said at least four point light sources reflected by a cornea;
    grouping a plurality of sets of combinations of said at least four point light sources, each set of combinations containing at least three of said point light sources;
    sequentially extracting positions of corneal reflection images of each set of combinations of point light sources detected;
    determining a part of a corneal shape by connecting the extracted positions of each set of corneal reflection images; and
    determining a total corneal shape based on each part of the corneal shape.

* * * * *